United States Patent
Foulger et al.

(10) Patent No.: US 6,946,086 B2
(45) Date of Patent: Sep. 20, 2005

(54) CHEMICAL COMPOSITIONS COMPRISING CRYSTALLINE COLLOIDAL ARRAYS

(75) Inventors: Stephen H. Foulger, Clemson, SC (US); Ping Jiang, Clemson, SC (US); Amanda C. Lattam, Clemson, SC (US); Travis Baughman, Gainesville, FL (US); John Ballato, Central, SC (US); Dennis W. Smith, Seneca, SC (US)

(73) Assignee: Clemson University, Clemson, SC (US)

( * ) Notice: Subject to any disclaimer, the term of this patent is extended or adjusted under 35 U.S.C. 154(b) by 608 days.

(21) Appl. No.: 09/998,922

(22) Filed: Nov. 30, 2001

(65) Prior Publication Data

US 2002/0118435 A1 Aug. 29, 2002

Related U.S. Application Data

(60) Provisional application No. 60/250,657, filed on Dec. 1, 2000.

(51) Int. Cl.[7] .......................... G02B 5/23; B01D 21/01; A61K 49/00; G01N 33/00; G01D 21/00
(52) U.S. Cl. ....................... 252/586; 516/99; 424/10.3; 436/116; 116/206
(58) Field of Search ............................. 252/582, 528; 516/99; 424/10.3; 436/116; 116/206; 350/362

(56) References Cited

U.S. PATENT DOCUMENTS

| | | | |
|---|---|---|---|
| 4,451,412 A | 5/1984 | Loisequx et al. | |
| 4,627,689 A | 12/1986 | Asher | |
| 4,632,517 A | 12/1986 | Asher | |
| 4,803,688 A | 2/1989 | Lawandy | |
| 5,131,736 A | 7/1992 | Alvarez | |
| 5,133,992 A | 7/1992 | Nair et al. | |
| 5,266,238 A | 11/1993 | Haacke et al. | |
| 5,368,781 A | 11/1994 | Haacke et al. | |
| 5,665,275 A | 9/1997 | Kobayashi et al. | |
| 5,737,102 A | 4/1998 | Asher | |
| 5,854,078 A | 12/1998 | Asher et al. | |
| 6,001,251 A | 12/1999 | Asher et al. | |
| 6,014,246 A | 1/2000 | Asher et al. | |
| 6,123,845 A * | 9/2000 | Asher et al. | 210/500.22 |
| 6,123,861 A * | 9/2000 | Santini et al. | 216/2 |
| 6,165,389 A * | 12/2000 | Asher et al. | 252/582 |
| 6,187,599 B1 * | 2/2001 | Asher et al. | 436/531 |
| 6,201,980 B1 | 3/2001 | Darrow et al. | |
| 6,339,030 B1 * | 1/2002 | Constant et al. | 438/758 |
| 6,444,254 B1 * | 9/2002 | Chilkoti et al. | 427/2.24 |
| 6,544,800 B2 * | 4/2003 | Asher | 436/531 |
| 6,632,922 B1 * | 10/2003 | Deming et al. | 530/333 |
| 6,753,191 B2 * | 6/2004 | Asher et al. | 436/531 |
| 2002/0164823 A1 * | 11/2002 | Asher et al. | 436/518 |

OTHER PUBLICATIONS

PCT Search Report, Dec. 2, 2002.

(Continued)

Primary Examiner—Randy Gulakowski
Assistant Examiner—Tim Kugel
(74) Attorney, Agent, or Firm—Dority & Manning, P.A.

(57) ABSTRACT

Crystalline colloidal arrays (CCA) which have been encapsulated in a polymer matrix to produce more robust polymerized crystalline colloidal arrays (PCCA) are provided. The PCCA's of the present invention can be in the form of a hydrogel which can be compatible for use with a biological system. The polymer matrix of the PCCA is formed of polymerized poly(ethylene glycol) based monomer units which can provide a desired functionality to the PCCA. The PCCA can be formed to exhibit a photonic bandgap at a certain wavelength. The photonic bandgap can be capable of shifting upon some form of environmental stimulation rendering the PCCA suitable for many optical applications, including active photonic switching and sensory applications.

34 Claims, 5 Drawing Sheets

OTHER PUBLICATIONS

Foulger, Stephen H. et al., Robust polymer colloidal crystal photonic bandgap structures, pp. 1300–1302, Optic Letters, vol. 25, No. 17. Optical Society of America, Sep. 1, 2000.

Xia, Younan et al., Monodispersed Colloidal Spheres: Old Materials with New Applications, pp. 693–713. Advanced Materials, 12, No. 10, 2000.

Asher, Sanford A. et al., Mesoscopically Periodic Photonic–Crystal Materials for Linear and Nonlinear Optics and Chemical Sensing, pp. 44–50. Mrs Bulletin, Oct. 1998.

Weissman, Jesse M. et al., Thermally Switchable Periodicities and Diffraction from Mesoscopically Ordered Materials, pp. 959–960. Science, New Series, vol. 274, Issue 5289 (Nov. 8, 1996).

Pan, Guisheng et al., Nanosecond Switchable Polymerized Crystalline Colloidal Array Bragg Diffracting Materials, pp. 6525–6530. J. Am. Chem. Soc. 1998, 120.

Asher, Sanford A. et al., Self–Assembly Motif for Creating Submicron Periodic Materials, Polymerized Crystalline Colloidal Arrays, pp. 4997–4998. J. Am. Chem. Soc. 1994, 116.

Sunkara, H.B. et al., Lattice dynamics of colloidal crystals during photopolymerization of acrylic monomer matrix, pp. 887–894. Journal of Materials Science, 33 (1998).

Jethmalani, Jagdish M. et al., Diffraction of Visible Light by Ordered Monodisperse Silica–Poly(methyl acrylate) Composite Films, pp. 2138–2146. Chemistry of Materials, vol. 8, No. 8.

Jiang, P. et al., Single–Crystal Colloidal Multipayers of Controlled Thickness, pp. 2132–2140. Chem. Mater. 1999, 11.

Carlson, Roger J. et al., Characterization of Optical Diffraction and Crystal Structure in Monodisperse Polystyrene Colloids, pp. 297–304. Applied Spectroscopy, vol. 38, No. 3, 1984.

Liu, Lei et al., Crystalline Colloidal Array of Water Voids in Hydrogels: Direct Evidence for Entropic Trapping of Flexible Polymers, pp. 4040–4046. J. Am. Chem. Soc. 1999, 121.

Rundquist, Paul A. et al., Dynamical Bragg diffraction from crystalline colloidal arrays, pp. 4932–4941. J. Chem. Phys., vol. 91,No. 8, 15.

Reese, Chad E. et al., Development of an Intelligent Polymerized Crystalline Colloidal Array Colorimetric Reagent, pp. 5038–5042. Analytical Chemistry, vol. 73, No. 21, Nov. 1, 2001.

Holtz, John H. et al., Intelligent Polymerized Crystalline Colloidal Arrays: Novel Chemical Sensor Materials, pp. 780–791. Analystical Chemistry, vol. 70; No. 4, Feb. 15, 1998.

Jethmalani, Jagdish M. et al., Optical Diffraction from Silica–Poly(methyl methacrylate) Composite Films, pp. 2633–2640. Langmuir 1997, 13.

Jethmalani, Jagdish M. et al., Crystal Structures of Monidisperse Colloidal Silica in Poly(mythyl acrylate) Films, pp. 3338–3344. Langmuir 1997, 13.

Pu, Zhengcai et al., Mechanical properties of a poly(methyl acrylate) nanocomposite containing regularly–arranged silica particles, pp. 545–551. Polymer Bulletin, Springer–Verlag 1996.

* cited by examiner

CHEMICAL COMPOSITIONS COMPRISING CRYSTALLINE COLLOIDAL ARRAYS

CROSS REFERENCE TO RELATED APPLICATIONS

Priority is hereby claimed to Provisional U.S. Application Ser. No. 60/250,657 which is entitled: "MATRICES FOR ENCAPSULATION OF CRYSTALLINE COLLOIDAL ARRAYS" filed Dec. 1, 2000.

BACKGROUND OF THE INVENTION

Waves in a periodic medium undergo coherent interference by multiple scattering when their wavelengths are comparable to the period spacing of the medium. Often, this results in the generation of distinct directions for waves having a certain energy to propagate. Therefore, an array comparable in period to the wavelength of electromagnetic waves can provide an analog i.e., a "bandgap," which can act as a filter for a particular wavelength. Such arrays are the focus of international research and development efforts due to the tremendously broad range of applicability of optical systems.

A crystalline colloidal array (CCA) is one example of such a periodic medium. A CCA comprises a three-dimensionally ordered lattice that can be composed of almost any self-assembled monodisperse colloidal particles. These ordered systems can be fabricated to diffract electromagnetic radiation, including the visible spectrum. The diffraction characteristics of CCA systems is most accurately predicted through the application of dynamic diffraction theory, though Bragg's law is a reasonable approximation. Under certain conditions, these CCA's can exhibit a photonic bandgap over a narrow range of the spectrum. Such arrays hold promise as a practical route to generating optical photonic crystals, which may be employed in many optical applications, including active photonic switching and sensory applications.

CCA's are the focus of ongoing research and development. For example, a pending provisional application that is owned by the Assignee of the present application is U.S. Provisional Application No. 60/327074 filed Oct. 3, 2001. This application is directed to a tunable radiation filter which includes a highly ordered crystalline array of particles fixed in an essentially water-free matrix.

In the past, these materials have been developed in a liquid phase. Unfortunately, liquid phase CCA materials do not exhibit a high level of robustness or stability. For instance, a liquid phase CCA will undergo a transitory disordering when subjected to a mechanical shock, while a permanent disordering can be induced to occur with the introduction of ionic impurities.

Prior art publications describe methods of making solid filter materials that filter a predetermined wavelength band. For instance, U.S. Pat. No. 6,001,251 to Asher et al. discloses creating a colloidal structure composed of particles dispersed within a medium, and introducing a solvent thereto. The solvent is then evaporated and the remaining structure crystallizes.

Other prior art publications have been directed to methods for "tuning" CCA's to particular band gaps for specific filtration or sensory applications. For example, U.S. Pat. No. 6,014,246 to Asher et al. is directed to mesoscopically periodic materials that combine CCA self-assembly with the temperature induced volume phase transitions of various materials.

Due in part to problems in the past concerning the robustness of liquid-phase CCA's, these systems have had limited practical applicability. Attempts have been made to stabilize CCA's using various materials, but again, the systems have had limited practical applicability due to, for example, the nature of the stabilizing material. For example, various acrylamides have been used in the past to aid in stabilizing a CCA. Such materials, however, are ineffective in certain applications, such as certain biologically based applications. Thus, many prior art products and methods are inapplicable for a host of biologically based applications, including, for example, sensory applications involving recognition of various microorganisms.

As a result, a composition comprising a CCA which provides good mechanical and optical properties would be very desirable. Additionally, it would be desirable to develop a CCA system which can provide not only the robustness necessary for practical applications, but also be useful in biological applications.

SUMMARY OF THE INVENTION

In general, the present invention is directed to a composition of matter comprised of a CCA which has been encapsulated by a polymeric matrix. More specifically, the polymeric matrix can be composed of poly(ethylene glycol) based monomer units which have polymerized around the particles of a CCA. The CCA can be, for example, an electrostatically stabilized CCA.

In certain embodiments, the polymerized crystalline colloidal array (PCCA) thus produced can be biologically compatible.

In general, the polymeric matrix can be based on poly(ethylene glycol) based monomer units including one or more of any suitable poly(ethylene glycol) (PEG) based variants.

In one embodiment, the poly(ethylene glycol) based monomer units used in the PCCA of the present invention can have a general formula of:

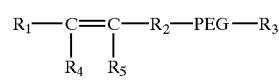

wherein the functional group $R_2$ can be any desired functional group having at least two active bonding sites, and the functional groups $R_1$, $R_3$, $R_4$, and $R_5$ can be any desired functional group. $R_1$, $R_4$ and $R_5$ can each be independently selected from any desired functional group including, for example, alkanes, alkenes, arenes, halides, ethers, acrylates, amine groups, amides, thiols, esters, ketones, nitro compounds, carboxy groups, hydroxy groups, or hydrogen. $R_3$ can likewise be any suitable functional group including, for example, alkanes, alkenes, arenes, halides, ethers, acrylates, amine groups, amides, thiols, esters, ketones, nitro compounds, carboxy groups, hydroxy groups, hydrogen, proteins, nucleotides, or antibodies. In one embodiment, the $R_2$ functional group can be an ester or a ketone group.

In certain embodiments, the functional group $R_3$ can be chosen to provide a specific biological functionality to the PCCA. For example, $R_3$ can be a protein, an antibody, or a nucleotide and designed to react with certain components of the PCCA environment.

In addition, the poly(ethylene glycol) group, denoted PEG, can be in either orientation, i.e. either as $(-CH_2CH_2-O-)_n$ or $(-O-CH_2CH_2-)_n$ within the monomer structure. For example, in one embodiment, the poly(ethylene glycol) monomer can be poly(ethylene glycol) methacrylate.

The colloidal particles used to form the CCA can be any suitable colloidal particles. For example, in one embodiment, the colloidal particles can be formed of polystyrene-based colloidal particles.

The polymerized matrix can be either a thermoset or a thermoplastic polymer matrix, as desired. For example, to form the desired polymer matrix, a crosslinking agent can be polymerized with the monomer in forming the matrix.

The PCCA of the present invention can exhibit a photonic bandgap at a certain wavelength of electromagnetic radiation. Upon some type of stimulation, the bandgap can be caused to shift, thus altering the perceived color of the PCCA.

Various types of environmental stimulation may cause the bandgap shift in the PCCA. For example, in one embodiment, the PEG monomer can include one or more specific functional groups designed to chemically react with components that may be encountered in the environment of the PCCA. This reaction could then cause a shift the in the bandgap of the PCCA.

Alternatively, other types of environmental stimulation can cause a bandgap shift in the PCCA. Various embodiments of the present invention are disclosed which can exhibit a bandgap shift due to, for example, thermal, electrical, chemical or mechanical stimulation of the disclosed composition. As such, the compositions of the present invention can be used in a wide variety of embodiments, including biologically compatible embodiments such as, for example, biologically compatible sensory devices.

BRIEF DESCRIPTION OF THE DRAWINGS

A full and enabling disclosure of this invention, including the best mode shown to one of ordinary skill in the art, is set forth in this specification. The following Figures illustrate the invention.

DETAILED DESCRIPTION OF THE INVENTION

It is to be understood by one of ordinary skill in the art that the present discussion is a description of exemplary embodiments only, and is not intended as limiting the broader aspects of the present invention, which broader aspects are embodied in the exemplary construction.

In general, the present invention is directed to CCA's which have been encapsulated in a polymer matrix to produce a more robust polymerized CCA (PCCA) in the form of an aqueous hydrogel. More particularly, a PCCA is provided which can be used in conjunction with a biological system, wherein the polymer matrix is formed of a water-soluble, biologically compatible monomer.

The PCCA's of the present invention may be formed of any suitable CCA. In general, a CCA is a three-dimensionally ordered lattice of self-assembled colloidal particles which can exhibit a photonic band gap. The colloidal particles employed in production of the array can be any desired colloidal particles which have at least one characteristic dimension. For example, the colloidal particles can be inorganic particles, such as an amorphous silica. Alternatively, the CCA can be formed of organic particles. Just a few examples of organic particles which have been used in the past to form CCA's include polystyrene, polymethyl methacrylate, polybutadiene, and polyisoprene, among many others. In general, any emulsion system including macro ions could be employed to form the CCA. In one embodiment, a CCA can be formed of a hybrid of two or more different particle types. For example, a CCA can be formed of a hybrid of two different types of organic particles or inorganic particles. Alternatively, a CCA can be formed of a hybrid of both inorganic and organic particles. In general, the macro ions utilized can be spherical in shape, though this is not a requirement.

A CCA will usually fall into one of two general categories. For example, a CCA can be a sterically packed array, in which the colloidal particles can usually be from about 10 nm to about 1 $\mu$m in diameter. Specifically, the particles can be from about 50 to about 800 nm in diameter. More specifically, the particles can be from about 200 to about 500 nm in diameter. Whatever the chosen diameter of the particles, the particles can contact each other to form an ordered, packed system.

Figure 1:
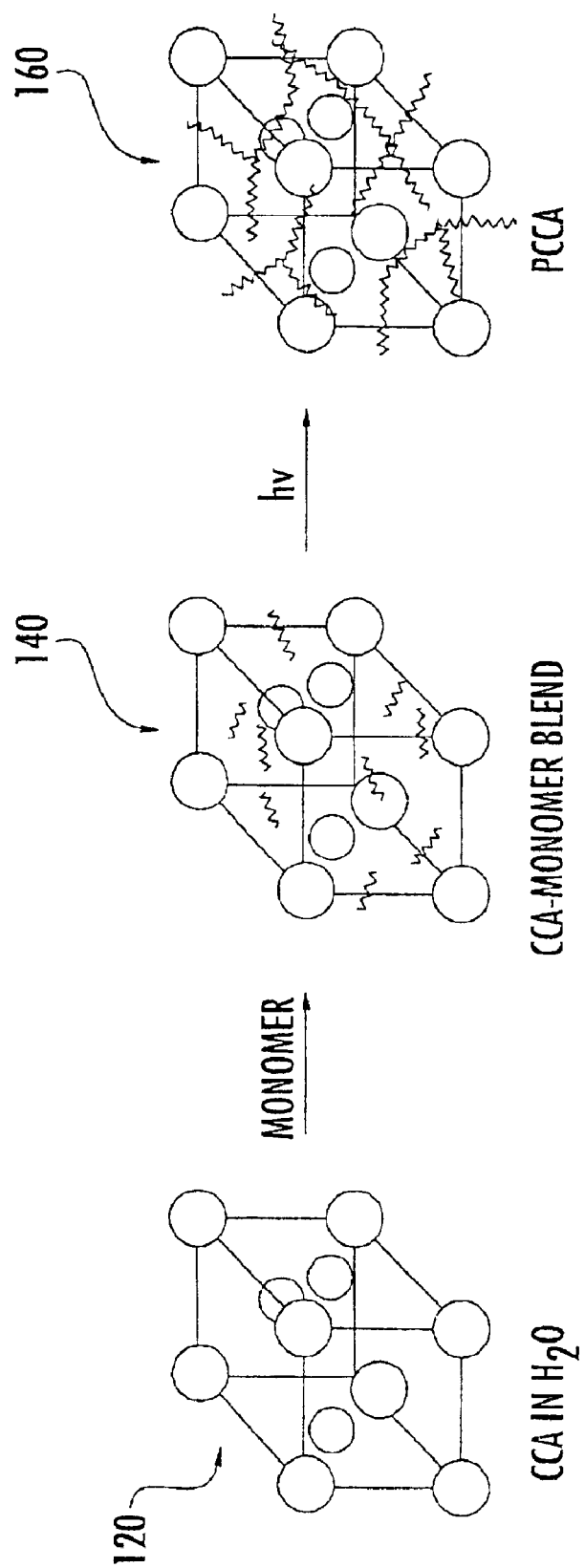
FIG. 1 is a schematic showing one method for stabilizing CCA's through encapsulation in a polymeric matrix.
Figure 2:
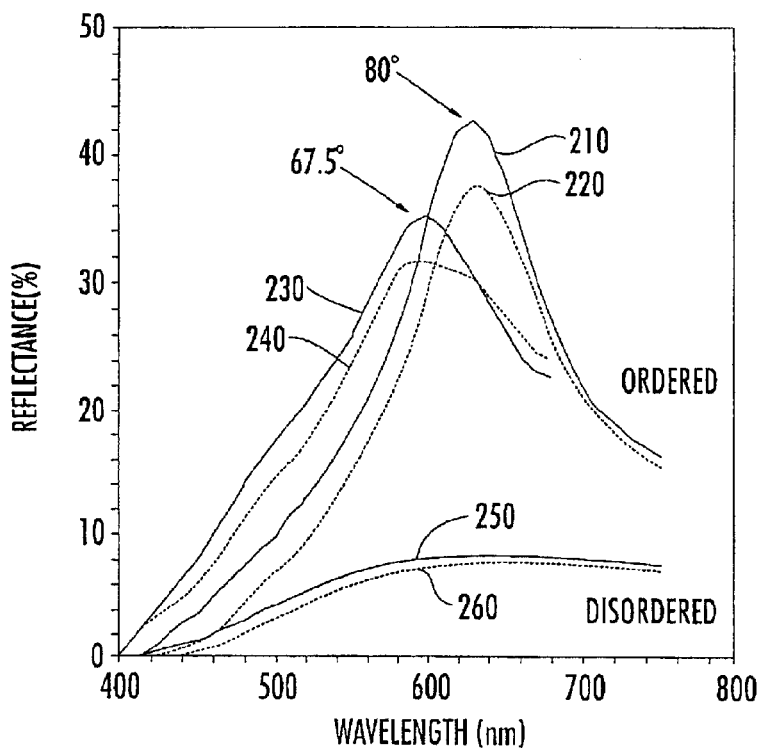
FIG. 2 shows reflectance spectra at two different Bragg angles of CCA/macromolecule blends and PCCA composites.

Alternatively, a CCA can be an electrostatically stabilized system, in which the colloidal particles are produced such that they exhibit a negative surface charge. When placed in a solution which is pure and nearly free of ionic species, the repulsive interaction between the macro ions can be significant over distances greater than 1 $\mu$m. When dispersed in a polar medium at high particle concentrations (greater than about $10^{13}/cm^3$), interactions between the surface charge of the particles, coupled with the consequent diffuse counterion cloud (known as a double layer effect) can result in the adoption of a minimum energy crystalline colloidal structure having either a body centered cubic (bcc) or face centered cubic (fcc) symmetry. Referring to FIG. 1, the typical structure of an electrostatically stabilized CCA, 120, is illustrated.

These CCA systems can be fabricated to exhibit specific periodicity analogous to electromagnetic wavelengths. For example, the periodicity of the array can be analogous to electromagnetic wavelengths in the infrared, visible, or ultraviolet spectrums. This can result in the appearance of a bandgap in the spectrum. The refractive index of these systems can be further adjusted through the addition of various additives. For example, dyes, photochromic dyes, or fluorine can be incorporated into the CCA to "tune" the optical effects of the system. CCA's exhibiting optical bandgap effects can then be employed in a variety of active photonic switching and sensory roles.

The PCCA's of the present invention have generally been formed from electrostatically stabilized CCA systems. In one embodiment, the CCA's utilized can be formed using monodisperse cross-linked polystyrene-based particles as the colloidal particles, though this is not required for practice of the invention. These particles can be prepared by using standard emulsion polymerization procedures which are known in the art. (See for example, *Advanced Materials*, 2000, 12, No. 10, "Monodispersed colloidal spheres: old material with new Applications", by Younan Xia, Byron Gates, Yadong Yin, and Yu Lu, which is herein incorporated in its entirety by reference thereto.) The colloidal particles employed can be of any suitable particle size, but in general will be between about 10 nanometers to about 10 microns in diameter. Specifically, the particles can be between about 20 and about 500 nanometers in diameter. More specifically, the particles can be between about 100 and about 200 nanometers in diameter.

In one possible embodiment, the resulting latex produced by the emulsion polymerization procedures can be dialyzed against deionized water and then shaken with an excess of mixed bed ion-exchange resin to remove excess electrolyte. The CCA can then be allowed to self-assemble.

The diffraction characteristics of CCA systems is most accurately predicted through the application of dynamic diffraction theory, though Bragg's law is a reasonable approximation. The Bragg equation in vector form is:

$$\left|\frac{\bar{s}-\bar{s}_o}{\lambda/n}\right| = \frac{1}{d}$$

where $s_0$ is the primary beam and s is the diffracted beam, $\lambda$ is the wavelength in air, n is the average refractive index of the composite, and d is the interplanar spacing of the diffracting lattice planes.

Of importance to the present invention, a CCA can be "tuned" to exhibit some desired periodicity and exhibit a specific bandgap based on the interplaner spacing, d, of the diffracting lattice planes. Interplaner spacing in turn can be a function of the concentration of colloidal particles forming the CCA. In other words, the concentration of colloidal particles can be designed or altered in order that the CCA exhibit a specific bandgap.

Conversely, a shift in the observed bandgap of the system can be evidence of a shift in the interplaner spacing, d, of the ordered system. Such a shift in the ordered lattice structure may be attributable to some specific stimulation of the system. For example, when a CCA is formed in a deionized water system, the CCA can opalesce at a certain color due to the optical bandgap effect. If water or some other compound in the system is allowed to escape, due to, for example, evaporation, the observed bandgap can shift due to the increased concentration of the colloidal particles and the decreased interplaner spacing of the array. As such, the system will opalesce at a bluer hue due to the change in particle concentration.

Similarly, the addition of a compound to the system can cause a decrease in the concentration of colloidal particles and a relative increase in the interplaner spacing of the array, thus a red shift in the optical bandgap can be seen. As a result, such CCA's can be useful in various optical switching and sensing technologies.

Unfortunately, these liquid-phase systems can undergo disordering under relatively minor disturbing influences. The lack of mechanical robustness and stability has prevented many possible practical applications of the systems, including, for example, biological applications.

In accordance with the present invention, alternative matrices to extend the successful routes by which CCAs can be encapsulated with biological compatible, water miscible polymers have been developed. Two methodologies have been explored: (1) blending of the CCA with a high molecular weight biologically compatible hydrophilic macromolecule and (2) in situ polymerization of hydrophilic thermoplastic and thermoset biologically compatible polymers around the ordered arrays.

To this end high molecular weight molecules have been employed which include poly(ethylene glycol) (PEG) based variants. These biologically compatible systems can exhibit a high degree of mechanical stability in their encapsulated form (PCCA) relative to the CCA while maintaining the CCA optical characteristics. In addition, these biologically compatible systems can exhibit an increased viscosity in their blended CCA/macromolecule form which can result in a reduction of the sensitivity of the CCA to minor mechanical disturbances.

In general, a CCA/macromolecule blend is the product of a CCA which has been suitably mixed with any desired macromolecule in the presence of an ion exchange resin to form a blended solution. FIG. 1 illustrates a schematic view of a typical CCA/macromolecule blend 140.

In order to produce a CCA/macromolecule blend system, the macromolecule chosen to be incorporated into the blend can be any suitable macromolecule which will not prevent the formation of the CCA. In one embodiment, the macromolecule can be chosen based on desired functional groups on the macromolecule. The functional group can be chosen for purposes of, for example, polymerizing the macromolecules into a matrix and/or reacting the macromolecule with some aspect of the CCA environment. For example, the macromolecule can include a functional group capable of reacting with a possible component of the CCA environment. Upon reaction of the functional group, a shift in interplanar spacing of the diffracting lattice planes can occur, which can lead to a shift in the visible CCA bandgap. Therefore, a change in color of the CCA can be evidence of the presence of the environmental component. Such a reaction could be due to a variety of environmental stimuli: chemical, thermal, electrical, mechanical, etc.

Alternatively, the macromolecule can merely provide structure and stability to the CCA such that the CCA itself can react directly to an environmental stimulus, such as external mechanical or electrical forces, for example, without losing its ordered structure; a loss which could otherwise occur barring the presence of the macromolecule. Upon reaction to the stimulus, the CCA can exhibit a visible alteration in the stop bandgap.

In one embodiment, various poly(ethylene glycol) (PEG) based polymers can be incorporated into the blend as the macromolecule. The PEG polymer chosen can have a high molecular weight, for example, the PEG can have a molecular weight as little as about 44 or as great as about 100,000. In one embodiment, the PEG can have a molecular weight of about 10,000. In an alternative embodiment, the PEG can have a molecular weight of between about 44 and about 3400. The amount of PEG added to the CCA can be any suitable amount which can increase the viscosity of the system in order to reduce the sensitivity of the CCA and still maintain the formation of the CCA. For example, the PEG can be added to the CCA from about 10 wt % by weight of the solution to about 80 wt % by weight of the solution. Particularly, the PEG can be added to the CCA from about 30 wt % to about 70 wt % by weight of the solution.

In order to further stabilize the CCA system, the macromolecule of the CCA/macromolecule blend can be chosen which can polymerize to form an encapsulating polymer matrix around the ordered particles of the CCA and produce a PCCA. For example, a PEG based variant can be utilized to form a CCA/PEG blend which can then polymerize to form a PCCA. The PCCA hydrogel composite thus produced can have greatly increased stability over the pure in aqueo CCA as well as over the CCA/PEG blend.

Referring to FIG. 2, Reflectance spectra are compared for ordered systems of a CCA/N,N-dimethylacrylamide blend and its PCCA composite at two Bragg angles as well as for a disordered blend and its polymerized hydrogel. As can be seen from the Figure, at a Bragg angle of 80°, the reflectance of the blended system, 210, is slightly higher than the polymerized system at 80°, 220, but there is little alteration in the diffraction characteristics of the system upon polymerization. This is true at a Bragg angle of 65° as well for both the blended system 230 and the polymerized system 240. When the system is disordered, i.e. the CCA has not formed, there is very little reflectance whether the system includes the polymerized matrix, 260, or is merely a blend of the polymerizable macromolecule and the colloidal particles, 250. Thus polymerizing the macromolecules of the blend to form an encapsulating matrix around the CCA can do little to effect the optical characteristics of the system, yet can greatly increase the robustness and stability of the CCA system.

In order to produce the desired PCCA, the pure CCA will first be blended with the monomer in the presence of an ion exchange resin and allowed to form an ordered, blended system. In addition to the monomer, other desired constituents can also be added to the blend. For example, in order to produce a more resilient, thermoset polymer matrix, a crosslinking agent may be included in the blend. Additionally, a polymerization initiator, such as, for example, a photoinitiator can be added. Also, other additives, such as various surfactants, dyes, or other reagents may be included in the blend.

In general, the polymeric matrix can be formed of any combination of any poly(ethylene glycol) based monomer units. For example, one or more different PEG based compounds could be blended together and included together in the final polymerized matrix.

In one embodiment, the poly(ethylene glycol) based monomer units used in the PCCA of the present invention can have a general formula of:

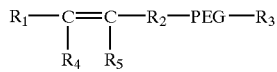

The only requirement of the functional group $R_2$ is that it include at least two active bonding sites, as is evidenced by the location of the group within the monomer. For example, $R_2$ can be, but is not limited to, oxygen, nitrogen, sulfur, or any suitable hydrocarbon groups. The functional groups $R_1$, $R_3$, $R_4$, and $R_5$ can each be any desired functional group. For example, $R_1$, $R_4$ and $R_5$ can each be independently selected from any desired functional group including, but not limited to, alkanes, alkenes, arenes, halides, ethers, acrylates, amine groups, amides, thiols, esters, ketones, nitro compounds, carboxy groups, hydroxy groups, or hydrogen. $R_3$ can likewise be any suitable functional group including, but not limited to, alkanes, alkenes, arenes, halides, ethers, acrylates, amine groups, amides, thiols, esters, ketones, nitro compounds, carboxy groups, hydroxy groups, hydrogen, proteins, nucleotides, or antibodies. Of course, all of the functional groups $R_1$, $R_2$, $R_3$, $R_4$, and $R_5$ can also be combinations of simpler groups.

In addition, the poly(ethylene glycol) group, denoted PEG, can be in either orientation, i.e. either as $(-CH_2CH_2-O-)_n$ or $(-O-CH_2CH_2-)_n$ within the monomer structure.

Possible monomers can include, but are in no way limited to, for example, poly(ethylene glycol) methyl ether methacrylate, poly(ethylene glycol) methacrylate, poly (ethylene glycol) methyl ether acrylate, poly(ethylene glycol) ethyl ether methacrylate, poly(ethylene glycol) monooleate, poly(ethylene glycol) acrylate, poly(ethylene glycol) behenyl ether methacrylate, poly(ethylene glycol) phenyl ether acrylate, and PEG based fluorinated acrylates.

In certain embodiments of the present invention, one or more of the functional groups, $R_1$, $R_2$, $R_3$, $R_4$, and $R_5$, can be chosen to provide some specific functionality to the PCCA. In such embodiments, the PCCA can be designed to react with certain environmental forces or components which can come into contact with the PCCA composite. For example, in one embodiment, an environmental component can chemically react with a functional group which can result in a change of the physical characteristics of the PCCA, including an alteration in the interplaner spacing of the array. This can in turn cause a shift in the visible bandgap of the PCCA. In such an embodiment, a PCCA can be utilized as a sensor for specific components which can chemically react with one of the functional groups.

In certain embodiments, the CCA/macromolecule blend and the PCCA produced by polymerization of a macromolecule around the ordered particles of a CCA can be suitable for biomedical applications, such as, for example, biomedical sensory applications. In order to work well in biomedical applications, a material should be biocompatible, that is, a material should neither destroy nor be destroyed by a biological system with which it will interact. In addition, a material should resist biofouling. Biofouling occurs when proteins irreversibly adsorb onto the surface of a material contacting the biological system. Poly(ethylene glycol) based variants are one material which have been found to work well in biomedical applications because they are not only biocompatible, but also resistant to biofouling. However, the present invention is not limited to the use of PEG based polymer matrices. For purposes of biomedical applications, other materials which can function with biological systems as well as polymerize around an ordered CCA to form a PCCA could also be utilized. Successful formation of a biocompatible PCCA allows for utilization of the present invention in countless biological applications.

In one possible embodiment of the present invention, one or more of the functional groups of the PEG based monomer could provide a specific biological activity to the PCCA. For example, the $R_3$ functional group of the PEG based variant can include one or more proteins, nucleotides, or antibodies which can chemically react with possible antigens, pathogens, microorganisms, etc. which could be found in the environment of the PCCA. Upon reaction, the interplanar spacing of the array can change, and cause a shift in the bandgap. In such an embodiment, a PCCA can be utilized as a sensory or switching device which, in the presence of some organism or chemical, can visibly change color.

In one embodiment, a PCCA can be capable of detecting the presence of various microorganisms, including, for example, viruses, spores, and bacteria. Such a sensory device could be an external device, such as a badge or a patch, formed to be worn on the clothing of a person or placed in a specific area.

Alternatively, a PCCA could be formulated to function within a biological system. For example, a PCCA could be an embeddable sensor which could be used to detect the presence of toxins, such as heavy metals, alcohol, or illegal drugs, or certain pathogens. In yet another embodiment, the PCCA could be an embeddable sensor which could be used to monitor the level of a body chemical, such as, for example, glucose or blood oxygen level. In such internal sensory embodiments, the sensor could be one in which the color change of the PCCA is visible to the user, i.e. at or near the skin surface. Alternatively, the PCCA could function as an electrical switch within the body, with the change in the hydrogel being communicated to a remote, external device, such as through an electrical switching and communication device.

Of course, the environmental stimulation leading to a visible shift in stop bandgap is not limited to a chemical stimulation of a specific functional group on the monomer. Other stimuli, such as, for example, thermal, mechanical, electrical or other chemical stimuli can react with either the encapsulating matrix or the encapsulated CCA itself to cause a visible shift in stop bandgap. For example, a mechanical stimulation, such as the application of strain to the PCCA can provide the necessary stimulation to alter the photonic bandgap of the PCCA.

Additionally, the present invention is not limited to biological sensory embodiments. The PEG based PCCA's of the present invention can be suitable for many other active photonic switching and sensory applications such as, for example, optical filters, optical limiters, membrane filters, optical switches, display devices and processing elements.

Referring again to FIG. 1, the monomer can be polymerized to form an encapsulated array 160. The PCCA can be formed by any suitable method. In general, such methods can be thin film formation methods. This could include lithography methods, such as, for example, photolithography, various forms of near-field optical lithography, and soft lithography. Alternatively, other forms of thin film formation could be utilized such as surface templating, layer-by-layer assembly methods, pulsed laser deposition methods, or through polymerization of the CCA/monomer blend solution within a defined area. For example, in one embodiment, the CCA/monomer solution can be an aqueous solution including a photoinitiator injected between two quartz plates separated by a Parafilm spacer and then polymerized into a PCCA hydrogel through exposure to an ultraviolet electromagnetic radiation source for a suitable period of time. In general, no matter what method of production is used, the product PCCA can have a size defined by the desired final application of the film. For example, the PCCA film can be from about 1 to about 1500 µm thick and have length and width dimensions as required.

To provide for more efficient polymerization of the monomer, a polymerization initiator can be added to the CCA/monomer blend. For example, in one embodiment, the polymerization process can be a photopolymerization process. Photopolymerization, though not required, has proven effective due to the limitation of possible disturbing forces which could disrupt the ordered system. In this particular embodiment, a photoinitiator can be added to the CCA/monomer blend. Any suitable photoinitiator can be used such as, for example, benzoin methyl ether (BME) or 2,2'-diethoxyacetophenone (DEAP). Usually, only a small amount of a photoinitiator is necessary for polymerization of the monomer to occur. For example, ratios of photoinitiator to monomer can be from about 1:100 to about 5:100 to effect polymerization as desired.

Upon polymerization, the polymer can form either a thermoplastic or a thermoset network, as desired, around the ordered colloidal particles. If a thermoset polymerized system is desired, a crosslinking agent may be added to the CCA/monomer blended system prior to polymerization. In general, a crosslinking agent can be added to the monomer in a ratio of from about 1:5 to about 1:20 (crosslinking agent to monomer). More specifically, the ratio of crosslinking agent to monomer can be from about 1:8 to about 1:15.

Any suitable crosslinking agent can be utilized. In general, in an embodiment involving a PEG based PCCA, the crosslinking agent can also be a PEG based agent, though this is not a requirement. A non-exhaustive list of possible crosslinking agents can include, but is not limited to: poly(ethylene glycol) dimethacrylate, poly(ethylene glycol) diacrylate, poly(ethylene glycol) divinyl ether, poly(ethylene glycol) dioleate, and N,N' methylene bis acrylamide.

The presence of as well as amount of a crosslinking agent can effect the final product PCCA characteristics. For example, if a more pliable, softer PCCA hydrogel film is desired, a thermoplastic network may be formed including no crosslinking agents at all. Alternatively, a crosslinking agent can be included in the polymer structure in amounts to effect the deformation characteristics of the product PCCA film. In either case, the encapsulation of the arrays with the polymer matrices can be sufficient to render a PCCA system not only stable to mechanical deformation, but can thereby enable the system to illicit a chromatic response under compressive loading. This can enable utilization of the PCCA systems in a variety of applications involving mechanical deformation of the film.

Figure 5:
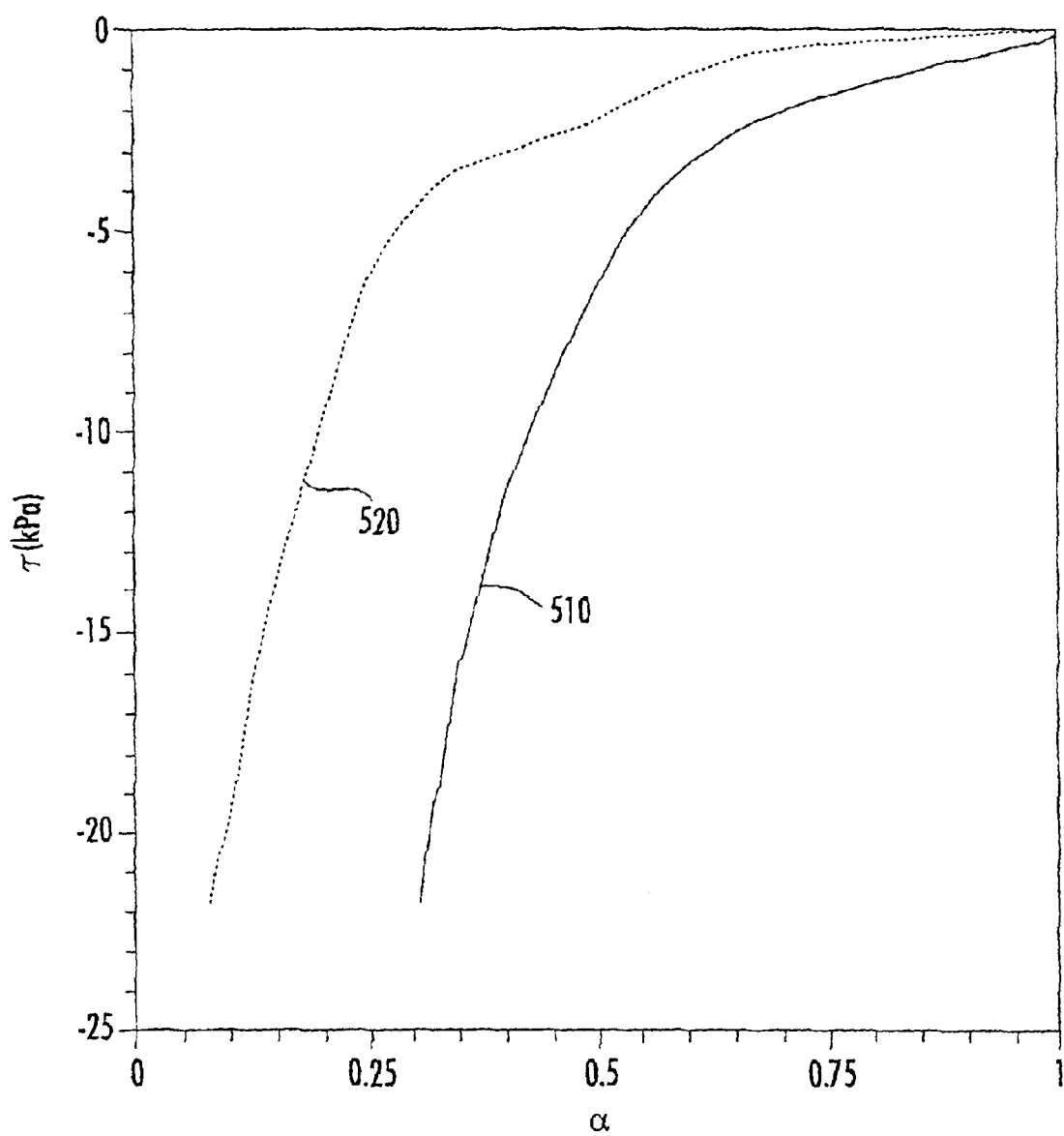
FIG. 5 shows a comparison of the mechanical response of PCCA and an unfilled hydrogel.

Referring to FIG. 5, the stress-strain response for a cross-linked PEG based PCCA composite (510) is compared to an unfilled hydrogel of the same formulation as the PCCA except that the CCA component has been replaced by water (520). In the Figure, $\tau$ is the force per unit area of hydrogel and $\alpha=h/h_o$ is the ratio of deformed sample height to initial height. In general, the mechanical behavior of these systems has been found to be similar to the general characteristic of rubber elastic behavior. For example, these systems can display high compressibility generated by a low mechanical stress that is completely recoverable.

As suggested in FIG. 5, the presence of the reinforcing polystyrene particles and lower water content in the PCCA composite 510 can result in a significantly higher modulus value and greater effective cross-link density relative to the values for the unfilled hydrogel 520. Nonetheless, the encapsulation of an array with a polymerized matrix can be sufficient to render the ordered array stable to mechanical deformation.

Figure 6:
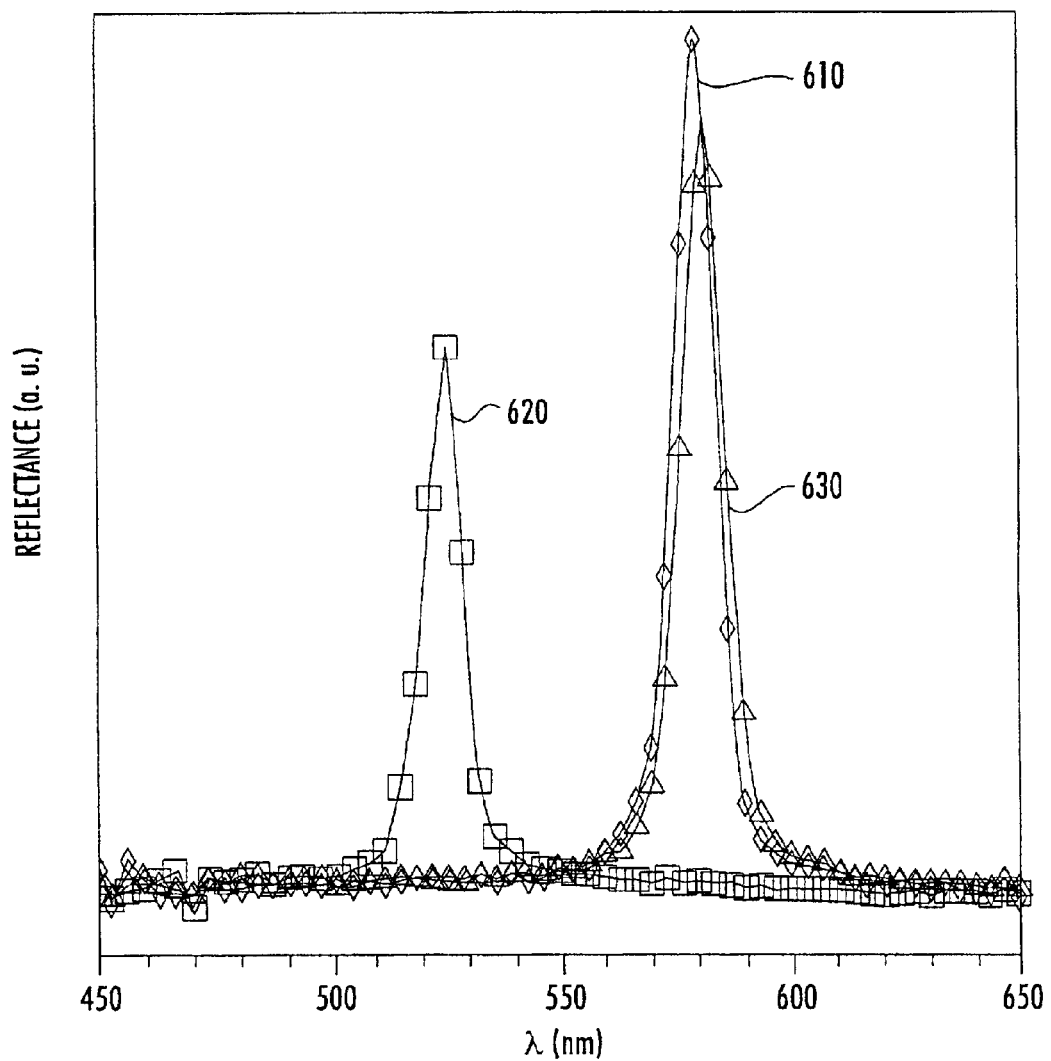
FIG. 6 shows the reflectance spectra of PCCA before, during and after application of a 1 kPa load.

Additionally, when the PCCA system is put under compressive forces such that mechanical deformation of the film occurs, the deformation can cause the film to exhibit color changes which can be proportional to the applied force. Referring to FIG. 6, the reflectance spectra of a water-swollen PCCA film before, during and after application of about 1 kPa compressive load is illustrated. In the original stress free state (610) the bandgap occurs at a wavelength of approximately 580 nm. Upon application of the compressive load, the bandgap shifts down to approximately 525 nm (620). This shift is due, it is believed, to a reduction in the distance between the colloidal particles in the array upon film deformation. Additionally, as can be seen in FIG. 6, the reflectance of the PCCA decreases upon deformation. It is speculated that the contraction of the lattice under loading introduces disorder which enhances the transmission at the photonic bandgap, thus reducing the reflectivity and causing the reflectance to decrease somewhat. Upon the removal of the load, however the film can immediately regain the optical characteristics of the original stress free state (630). Thus the PCCA's of the present invention can be utilized in applications involving deformation of the PCCA films.

The present invention demonstrates the potential for robust photonic bandgap structures made from polymeric systems which can be biologically compatible. This opens the door to a myriad of opportunities enabled through tailoring the optical functionality of the polymer CCA and matrix for task-specific photonic and optoelectronic applications.

Reference now will be made to possible embodiments of the invention, one or more examples of which are set forth below. Each example is provided by way of explanation of the invention, not as a limitation of the invention. In fact, it will be apparent to those skilled in the art that various modifications and variations can be made in this invention without departing from the scope or spirit of the invention. For instance, features illustrated or described as part of one embodiment can be used on another embodiment to yield a still further embodiment. Thus, it is intended that the present invention cover such modifications and variations as come within the scope of the appended claims and their equivalents.

EXAMPLE 1

A blend of a CCA and poly(ethylene glycol) monomer was prepared. The polythethylene glycol monomer utilized had a number average molecular weight ($M_n$) of about 10,000.

The following procedure was utilized to prepare the sample:
1) Obtained PEG solution (50 wt. % in deionized water) in a poly(methylmethacrylate) cuvette;
2) Added CCA to the cuvette;
3) Shook cuvette until complete mixing occurred;
4) Allowed sample to sit undisturbed until self-assembly of the CCA could be determined due to opalescence.

The sample was prepared including 0.75 g PEG in solution (50% in deionized water) and 0.82 g CCA. The PEG solution was added to the stable CCA and the mixture was shaken until complete mixing occurred. The CCA reformed after about 5 minutes.

EXAMPLE 2

Polymerized crystalline colloidal arrays (PCCA) were formed using CCA which was shaken for 2 hours with a poly(ethylene glycol) methacrylate (PEG-MA) monomer, poly(ethylene glycol) dimethacrylate (PEG-DMA) as a cross-linker, and diethoxyacetophenone (DEAP) as a photoinitiator over an ion exchange resin (AG® 501-X8(D)) to form a blend using deionized water as suspension.

The following experiment was performed, with results shown below.

| | |
|---|---|
| 1. CCA: crosslinked polystyrene | 1.00 ml |
| 2. PEG-MA: | 0.20 ml |
| 3. PEG-DMA: | 0.020 ml |
| 4. DEAP: | 0.0020 ml |

Items 1 to 4 referenced above were mixed in a glass vial and shaken with ion exchange resins for 24 hours. The opalescence could be observed in the glass vial upon self assembly of the CCA. Samples were then taken from the vial and put in two cuvettes separately. These samples were placed in a cuvett for five minutes, and the CCA crystal-like structure was observed. One of these samples was then polymerized under a UV lamp for 5 minutes A hydrogel was formed which showed opalescence (pink) inside.

Another sample was kept for over 7 days at room temperature. This liquid sample opalesced violet after 7 days. The sample was then polymerized under a UV lamp for 5 minutes. A hydrogel formed and showed opalescence (green) inside.

The chemical name and structure of components of PCCA referenced above are provided below:

1. CCA: Polystyrene spheres.

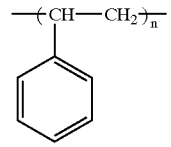

2. PEG-MA: Poly(ethylene glycol) methyacrylate, $M_n$: about 360

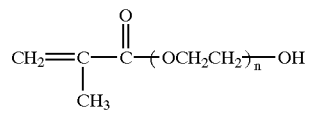

3. PEG-DMA: Poly(ethylene glycol) dimethyacrylate, $M_n$: about 550

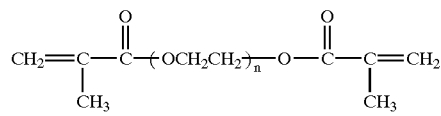

4. DEAP: 2,2'-diethoxyacetophenone:

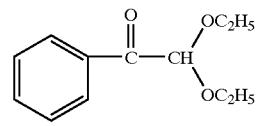

EXAMPLE 3

PCCA was prepared using deionized water as suspension as in Example 2. The formed matrices were prepared with either a poly(ethylene glycol) acrylate (PEG-A) monomer crosslinked with poly(ethylene glycol) diacrylate (PEG-DA) or else were formed using a poly(ethylene glycol) methacrylate (PEG-MA) monomer crosslinked with poly (ethylene glycol) dimethacrylate (PEG-DMA). All samples were polymerized using DEAP as a photoinitiator. The four samples are described below in Table 1.

TABLE 1

| Sample | CCA (g) | PEG-A (g) | PEG-DA (g) | PEG-MA (g) | PEG-DMA (g) | DEAP |
|---|---|---|---|---|---|---|
| 1 | 1.0 | 0.50 | 0.05 | | | 0.0050 |
| 2 | 1.0 | 0.20 | 0.02 | | | 0.0020 |
| 3 | 1.0 | | | 0.50 | 0.05 | 0.0050 |
| 4 | 1.0 | | | 0.20 | 0.02 | 0.0020 |

The opalescence of the CCA disappeared after adding the PEG variants. After adding the PEG variant and ion exchange resin the samples were shaken thoroughly.

After shaking, all samples #1–#4 again showed opalescence.

An attempt was made to polymerize sample #4 under UV light after the CCA appeared in the shaken vial. A portion of Sample #4 was placed in a cuvette and allowed to sit for five minutes. This sample was then photopolymerized under UV light for five minutes. A hydrogel with crystal-like (pink)

structure was formed in the cuvette, showing evidence of the CCA in the hydrogel matrix.

A portion of Sample #4 was placed in a cuvette for 7 days and opalesced a purple color, no crystal was seen. This portion was then subjected to UV light for 5 minutes and photopolymerization occurred. A green crystal-like structure was observed in the hydrogel.

EXAMPLE 4

Monodisperse polystyrene particles were prepared using an emulsion polymerization procedure. The resulting particle diameters were measured to be 159 nm with a Brookhaven BI-90 dynamic light scattering apparatus. The particles were dialyzed against de-ionized water for about 30 hours at 60° C. and then shaken with Bio-Rad™ AG 501-X8 mixed bed ion exchange resin. The cleaned suspensions were stored in Nalgene™ bottles to minimize contamination from ionic impurities. Matrix precursors and all other materials utilized were supplied by either Fisher Scientific or the Aldrich Chemical Company.

The CCA composites were injected between quartz or glass plates separated by a spacer of about 125 μm, and then polymerized in situ with a Blak-Ray™ UV lamp (Model B-100A). Extinction spectra were collected on a Shimadzu™ UV3101 UV/VIS/NIR spectrophotometer with the incident light normal to the plate surface. Reflectance spectra were obtained using a GreTag MacBeth™ CE741 UFV/VIS goniospectrometer.

Monodispersed polystyrene particles were dispersed in ion-exchange treated de-ionized water to form the initial CCA mesophase at a particle density of about $6.3 \times 10^{13}$ cm$^3$. Inert water soluble poly(ethylene glycol) (PEG), poly(ethylene glycol)-terminated methylmethacrylate (PEG-MMA), or N,N dimethylacrylamide was then added with and without a bisacrylamide crosslinker and photo-initiator (diethoxyacetophonone) in the presence of ion-exchange resin.

Stable blends of the CCA with the different monomers were then characterized by UV-visible spectroscopy and subsequently polymerized by exposing the blend to UV light (for acrylic precursors) which afforded cured photonic composites.

High molecular weight forms of PEG ($M_n$ of about 10,000) were used to assess the propensity of the CCA's to coexist in the presence of the hydrophilic polymer.

Figure 3:
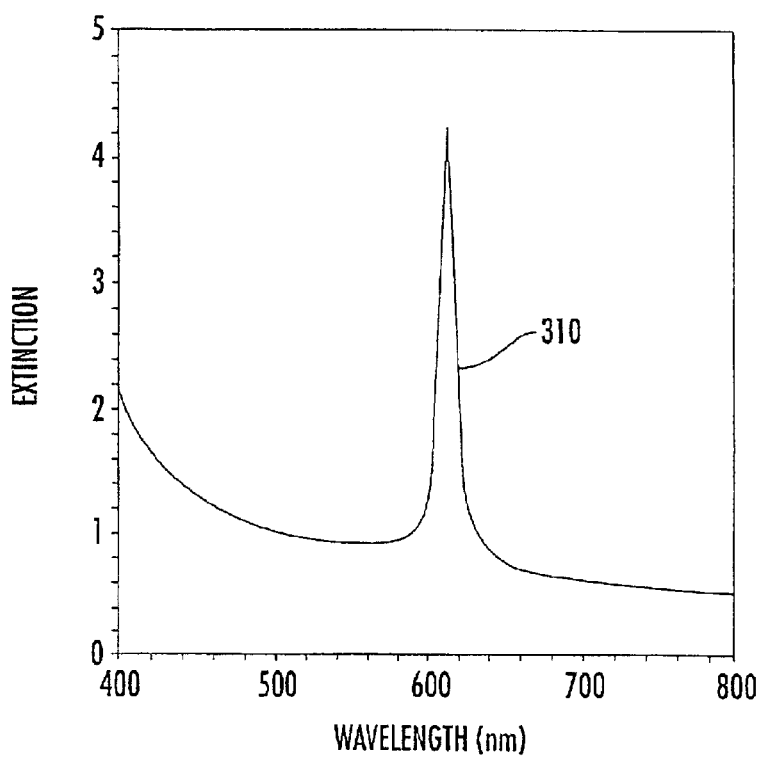
FIG. 3 shows extinction spectra of a CCA/PEG blend.

FIG. 3 presents the extinction spectra 310 of the CCA-PEG blend where the PEG has been incorporated into the CCA suspension at a 40 w/w level, resulting in a particle density of about $4.7 \times 10^{13}$ /cm$^3$. At this level of PEG incorporation, the solution blend exhibited a significantly increased viscosity relative to the "pure" CCA.

The diffraction characteristics of the CCA-PEG blend which is shown in FIG. 3 can be reasonably approximated with Bragg's law. Using Bragg's law and assuming a (111)-oriented fcc lattice results in a value of $d_{111}=224$ nm for the peak in FIG. 3 ($\lambda=614$ nm, n=1.37) and a resultant lattice constant of 388 nm, which corresponds to a nearest neighbor distance of 247 nm.

PEG-MMA with a $M_n=2080$ was combined with a CCA suspension as well as a photoinitiator of 2,2-diethoxyacetophenone. The mixture was injected into a glass plate assembly and polymerized by exposure to UV light for 5 minutes. The reflectance spectra of this blend before and after polymerization exhibited a single peak which was attributed to diffraction and is presented in Table 2 with the corresponding interplanar spacings. A disordered blend did not exhibit any reflectance peaks and was relatively uniform with wavelength. This disordered blend was produced by adding a minute amount of sodium hydroxide to the unpolymerized ordered blend, which resulted in an immediate cessation of opalescence. The peak, which is observed in the unpolymerized blend, is still apparent in the polymerized system, though altered in position. The origin of the slight shift from about 620 nm to about 660 nm upon polymerization is unclear. Nonetheless, it is clear that PEG based variants, which are polymerized in situ of the ordered arrays, are successful routes to producing PCCA composites.

TABLE 2

|  | θ | peak (nm) | d (nm) |
|---|---|---|---|
| CCA/PEG-MMA | 55E | 620 | 280 |
| PCCA/PEG-MMA | 55E | 660 | 298 |

θ is the Bragg angle of the incident beam relative to the diffracting plane. The refractive index of the composite was taken as 1.35.

EXAMPLE 5

Polymerized CCA's were prepared and examined according to the methods of Example 4, above. The Formulations of the mixture are summarized in Table 3, below.

TABLE 3

Formulation of CCA and CCA/PEG mixture (v/v)

|  | CCA | CCA/PEG |
|---|---|---|
| Polystyrene/water ($5.6 \times 10^{13}$ particles/cm$^3$) | 100 | 81.80 |
| Poly(ethylene glycol) methacrylate (PEG-MA) |  | 16.35 |
| Poly(ethylene glycol) dimethacrylate (PEG-DMA) |  | 1.65 |
| 2,2-diethoxyacetophenone (DEAP) |  | 0.20 |

Table 4 presents the resulting optical characteristics of the CCA, the CCA/PEG mixture, and the PCCA after exposure to a UV source for 4 minutes. The volume fraction (ψ) of the polystyrene particles, the refractive indices (n) the wavelength of the observed stop bands ($\lambda_o$) and the observed and calculated bandwidths are shown. According to phase diagrams of ordered colloidal suspension, the CCA and CCA/PEG mixture contained polystyrene volume fractions that would result in a fcc lattice. Bragg's diffraction equation was used to relate the observed stop band to the lattice parameter of the conventional cubic unit cell through $a_c=3d_{111}$ while the nearest neighbor distance $a=a_c/2$.

TABLE 4

|  | CCA | CCA/PEG | PCCA |
|---|---|---|---|
| $\Psi_{polystyrene}$ | 0.0510 | 0.0412 | 0.0416 |
| $n_{matrix}$ | 1.331 | 1.358 | 1.358 |
| $n_{composite}$ | 1.344 | 1.367 | 1.368 |
| $\lambda_{o(nm)}$ | 498.0 | 544.1 | 542.3 |
| Bandwidth$_{observed}$ | 15.0 | 12.5 | 13.0 |
| bandwidth$_{theoretical}$ | 8.4 | 6.7 | 6.87 |
| $d_{111}$(nm) | 185.2 | 198.9 | 198.3 |
| $a_c$(nm) | 320.9 | 344.6 | 343.4 |
| a(nm) | 226.9 | 243.7 | 242.8 |

Figure 4:
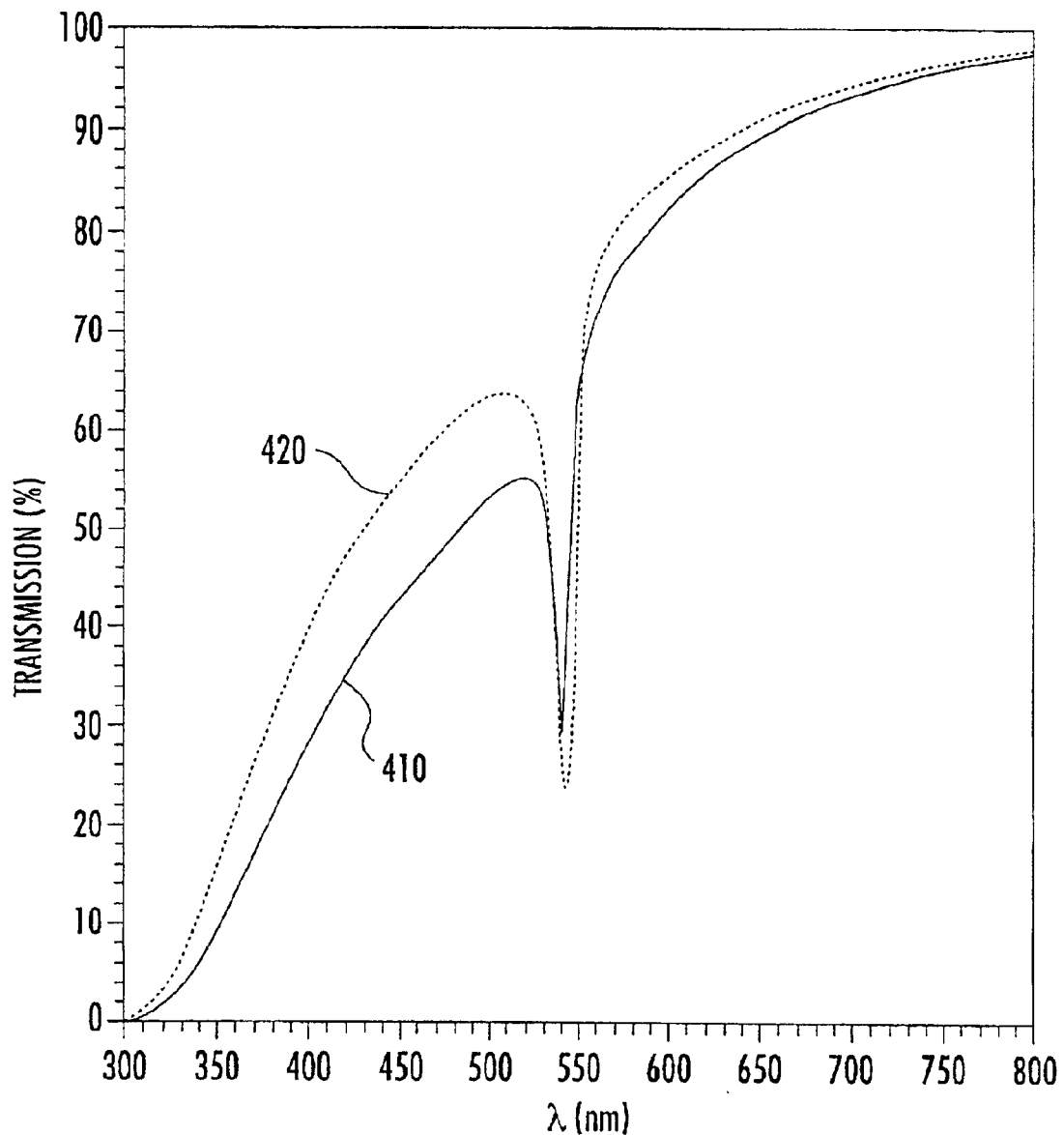
FIG. 4 shows transmission spectra of CCA/PEG blend and the corresponding PCCA composite with normal incident light.

FIG. 4 presents the transmission spectra of the CCA/PEG mixture (420) and its resulting composite after the mixture has been photopolymerized (410). The PCCA composite exhibited a decrease of about 2 nm in the wavelength of the stop band and a slight increase in the bandwidth relative to the liquid CCA/PEG mixture. In addition, the pass bands exhibit a decrease in transmission for the composite, relative to the mixture, with the decrease being significant at shorter wavelengths.

These and other modifications and variations to the present invention may be practiced by those of ordinary skill in the art, without departing from the spirit and scope of the present invention, which is more particularly set forth in the appended claims. In addition, it should be understood that aspects and various embodiments may be interchanged both in whole or in part. Furthermore, those of ordinary skill in the art will appreciate that the foregoing description is by way of example only, and is not intended to limit the invention so further described in such appended claims.

What is claimed is:

1. A composition comprising:
   a crystalline colloidal array comprising ordered particles; and
   a polymeric matrix encapsulating said crystalline colloidal array, wherein said polymeric matrix comprises polymerized poly(ethylene glycol) based monomer units polymerized among the ordered particles of the crystalline colloidal array.

2. The composition of claim 1, wherein said composition is biologically compatible.

3. The composition of claim 1, wherein said crystalline colloidal array is electrostatically stabilized.

4. The composition of claim 1, wherein said poly(ethylene glycol) based monomer units have a general formula of:

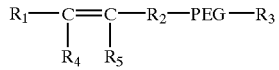

wherein $R_2$ comprises a functional group having at least two active bonding sites, $R_1$, $R_4$ and $R_5$ are each independently selected from the group consisting of alkanes, alkenes, arenes, halides, ethers, acrylates, amine groups, amides, thiols, esters, ketones, nitro compounds, carboxy groups, hydroxy groups, and hydrogen, and $R_3$ is selected from the group consisting of alkanes, alkenes, arenes, halides, ethers, acrylates, amine groups, amides, thiols, esters, ketones, nitro compounds, carboxy groups, hydroxy groups, hydrogen, proteins, nucleotides, and antibodies.

5. The composition of claim 4, wherein $R_2$ is selected from the group consisting of ketones and esters.

6. The composition of claim 5, wherein said poly(ethylene glycol) based monomer comprises poly(ethylene glycol) methacrylate.

7. The composition of claim 4, wherein $R_3$ is selected from the group consisting of proteins, nucleotides, and antibodies.

8. The composition of claim 1, wherein said crystalline colloidal array comprises polystyrene-based colloidal particles.

9. The composition of claim 1, further comprising a crosslinking agent polymerized with said polymeric matrix.

10. The composition of claim 1, wherein upon receiving electromagnetic radiant energy said composition exhibits a visible photonic bandgap.

11. The composition of claim 10, wherein said visible photonic bandgap is capable of shifting upon environmental stimulation of said composition.

12. A composition comprising:
   a crystalline colloidal array comprising ordered polystyrene-based colloidal particles in an aqueous medium; and
   a polymeric matrix encapsulating said crystalline colloidal array, wherein said polymeric matrix comprises polymerized poly(ethylene glycol) based monomer units represented by:

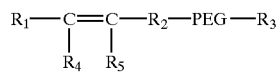

wherein $R_2$ comprises a functional group having at least two active bonding sites, $R_1$, $R_4$ and $R_5$ are each independently selected from the group consisting of alkanes, alkenes, arenes, halides, ethers, acrylates, amine groups, amides, thiols, esters, ketones, nitro compounds, carboxy groups, hydroxy groups, and hydrogen, $R_3$ is selected from the group consisting of alkanes, alkenes, arenes, halides, ethers, acrylates, amine groups, amides, thiols, esters, ketones, nitro compounds, carboxy groups, hydroxy groups, hydrogen, proteins, nucleotides, and antibodies, and a crosslinking agent polymerized with said monomer units, wherein said monomer units are polymerized among the ordered particles of the crystalline colloidal array.

13. The composition of claim 12, wherein said composition is biologically compatible.

14. The composition of claim 12, wherein $R_2$ is selected from the group consisting of ketones and esters.

15. The composition of claim 12, wherein said poly(ethylene glycol) based monomer comprises poly(ethylene glycol) methacrylate.

16. The composition of claim 12, wherein $R_3$ is selected from the group consisting of proteins, nucleotides, and antibodies.

17. The composition of claim 12, wherein upon receiving radiant energy said composition exhibits a visible photonic bandgap.

18. The composition of claim 17, wherein said visible photonic bandgap is capable of shifting upon environmental stimulation of said composition.

19. A sensory device comprising:
   a crystalline colloidal array comprising an ordered lattice structure defining a visible bandgap at a first wavelength;
   a polymerized matrix encapsulating said crystalline colloidal array, said polymerized matrix comprising poly(ethylene glycol) based monomer units polymerized among the ordered lattice structure of the crystalline colloidal array; and
   wherein upon stimulation of said sensory device said visible bandgap is capable of shifting to a second wavelength.

20. The sensory device of claim 19, wherein said sensory device is biologically compatible.

21. The sensory device of claim 19, wherein said poly(ethylene glycol) based monomer units are represented by:

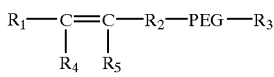

wherein $R_2$ comprises a functional group having at least two active bonding sites, $R_1$, $R_4$ and $R_5$ are each independently selected from the group consisting of alkanes, alkenes, arenes, halides, ethers, acrylates, amine groups, amides, thiols, esters, ketones, nitro compounds, carboxy groups, hydroxy groups, and hydrogen, and $R_3$ is selected from the group consisting of alkanes, alkenes, arenes, halides, ethers, acrylates, amine groups, amides, thiols, esters, ketones, nitro compounds, carboxy groups, hydroxy groups, hydrogen, proteins, nucleotides, and antibodies.

22. The sensory device of claim 21, wherein said wavelength shift is defined by a chemical reaction between said poly(ethylene glycol) based monomer units and an environmental component.

23. The sensory device of claim 22, wherein $R_3$ is selected from the group consisting of proteins, nucleotides, and antibodies.

24. The sensory device of claim 19, wherein said wavelength shift is defined by a mechanical stimulation of said sensory device.

25. The sensory device of claim 19, wherein said wavelength shift is defined by a thermal stimulation of said sensory device.

26. The sensory device of claim 19, wherein said wavelength shift is defined by an electrical stimulation of said sensory device.

27. The sensory device of claim 19, wherein said wavelength shift is defined by a chemical stimulation of said sensory device.

28. A composition comprising:

an aqueous solution comprising a high molecular weight poly(ethylene glycol) based macromolecule in a concentration such that the viscosity of the solution is increased due to the presence of the macromolecule concentration; and a crystalline colloidal array within the aqueous solution.

29. The composition of claim 28, wherein the poly (ethylene glycol) based macromolecule has the general formula:

wherein $R_1$ and $R_2$ are independently selected from the group consisting of alkanes, alkenes, arenes, halides, ethers, acrylates, amine groups, amides, thiols, esters, ketones, nitro compounds, carboxy groups, hydroxy groups, hydrogen, proteins, nucleotides, and antibodies.

30. The composition of claim 28, wherein said crystalline colloidal array comprises polystyrene-based colloidal particles.

31. The composition of claim 28, wherein upon receiving electromagnetic radiant energy said composition exhibits a visible photonic bandgap.

32. The composition of claim 28, wherein said visible photonic bandgap is capable of shifting upon environmental stimulation of said composition.

33. The composition of claim 28, wherein the concentration of the macromolecule is between about 10% and about 80% by weight of the solution.

34. The composition of claim 28, wherein the poly (ethylene glycol) has a molecular weight between about 10,000 and 100,000.

* * * * *